United States Patent [19]
Hartmeister et al.

[11] Patent Number: 5,389,099
[45] Date of Patent: Feb. 14, 1995

[54] KEYHOLE ROD BENDER

[76] Inventors: Ruben Hartmeister, 900 Washington Ave.; Walter E. Strippgen, 4960 McIntyre, both of Golden, Colo. 80401

[21] Appl. No.: 98,804
[22] Filed: Jul. 28, 1993
[51] Int. Cl.⁶ .................. B21J 13/08; B21D 53/00
[52] U.S. Cl. .................. 606/61; 606/101; 7/166; 81/15.9
[58] Field of Search .................. 606/61, 101; 7/166; 81/15.9

[56] References Cited

U.S. PATENT DOCUMENTS

| | | |
|---|---|---|
| 2,737,835 | 3/1956 | Herz . |
| 2,800,818 | 6/1957 | Larson . |
| 3,680,834 | 8/1972 | Holloway .................. 7/166 |
| 3,819,221 | 6/1974 | O'Connor .................. 81/15.9 |
| 3,866,458 | 2/1975 | Wagner . |
| 3,965,720 | 6/1976 | Goodwin et al. . |
| 4,034,595 | 7/1977 | Smith . |
| 4,444,228 | 4/1984 | Demirjian . |
| 4,917,154 | 4/1990 | Roberson, Sr. . |
| 5,113,685 | 5/1992 | Asher et al. . |

Primary Examiner—Stephen C. Pellegrino
Assistant Examiner—Sonya C. Harris
Attorney, Agent, or Firm—Rick Martin

[57] ABSTRACT

A pair of surgical in situ rod benders having keyhole notches to prevent slipping off the rod while in use. The in situ benders also have a 20° offset angle to allow a criss-cross pushing tension during bending. A flat tapered handle helps the surgeon counter rotational torques during bending.

18 Claims, 6 Drawing Sheets

KEYHOLE ROD BENDER

FIELD OF INVENTION

The present invention relates to improvements to in situ rod benders used in back surgery.

BACKGROUND OF THE INVENTION

The human spine normally has contours in the sagital (vertical) plane. A deformed spine may have contours in the coronal (horizontal) plane and/or the axial (rotational) plane. It has become a common surgical practice to insert one or two rods in the spine to straighten a deformed spine. Bone screws are placed in the pedacles of the backbone to secure the rods. The rods are pre-bent to the approximate corrective angles as taught by U.S. Pat. No. 5,113,685 (1992) to Asher et al. The rods are then inserted into the backbone and secured with clamps to the bone screws.

At this stage in the surgical procedure there needs to be made in situ adjustment bends to the rod(s). Space to access the rod(s) is at a premium. The clamps are usually spaced about four inches apart. The lamina (ridges) of the backbone complicate access to the rod(s). The rod(s) are full of blood and are slippery.

The rods are usually $\frac{1}{4}$ inch in diameter and constructed of stainless steel. In situ bending also requires moving the rib cage and large portions of body mass. It takes all the strength of a surgeon to bend the rods even with the use of fifteen inch bending tools. If the bending tools slip off the rod during the in situ bending procedure, then injury to the patient can occur.

Known in the art is the Isola ® In Situ Bender Model 2060-30 manufactured by Acromed. FIG. 1 shows the right hand Model 2060-30 bender 1. It is a stainless steel instrument having a tubular handle 2. A portion of the handle 2 has knurls 3. The working ends 4,6 are offset an angle $\theta_1$ of about 10°. Working end 4 has rod slot 5. $W_2$ is $\frac{1}{4}$ inch to accommodate a $\frac{1}{4}$ inch stainless steel rod. A rod slot (not shown) on working end 6 has a width of 3/16 inch for a 3/16 inch rod. Each rod slot has a single central bore (B—B for rod slot 5).

In operation to grasp a rod (not shown) the rod slot 5 is placed on the rod, and a left bender (not shown) is placed at a desired point on the same rod. The surgeon then pushes or pulls the benders to obtain the desired bend.

There are no means to secure the rod inside the rod slot 5 during the bending procedure. Thus, the rod is prone to slip out of the rod slot 5 during the bending procedure. This can injure a patient.

The present invention adds two additional bores besides the central axis bore B—B. Each additional bore is at about a 3° angle off axis to B—B. This creates a keyhole notch which helps secure the rod during the bending operation. Additionally a new flat handle is provided rather than a tubular handle. This flat handle helps the surgeon to overcome rotational forces on the handle. The angle $\theta_1$ of about 10° is also increased to about 20°. This permits a criss-crossing of the benders. The surgeon now has the option of squeezing or pushing the benders together rather than pulling them apart.

The dimensions of the prior art shown in FIG. 1 are as follows:
$\theta_1 = 10°$
$W_2 = \frac{1}{4}''$
$W_1 = 7/16''$
$d_1 = 13\frac{1}{2}''$
$d_2 = \frac{3}{4}''$

SUMMARY OF THE INVENTION

The primary object of the present invention is to provide a keyhole in the rod slot of benders to secure a rod during the bending procedure of the rod.

Another object of the present invention is to provide flat, tapered handles on a rod bender to help counter rotational torque.

Another object of the present invention is to provide approximately a 20° offset on the working ends of a rod bender to allow criss-crossing the benders, thereby enabling pushing the handle ends together.

Other objects of this invention will appear from the following description and appended claims, referenced being had to the accompanying drawings forming a part of this specification wherein like reference characters designate corresponding parts in the several views.

The keyhole rod bender improves upon the prior art for in situ benders by adding two additional center bores at 3° off axis in the rod slot. The result is a small keyhole shape in the bottom of the rod slot. These semi-circular seats form an area of contact with the rod in the shape of a frustum of a cone. It is understood that each bore is the same size as the rod. When the benders are under tension while grasping a rod, the keyhole helps to prevent the rod from slipping out of the rod slot. Surgeons are not mechanics who use tools eight hours a day. The keyhole rod bender helps to reduce the odds of a dangerous slip off the rod.

To further help the surgeon the rod handle is flat and tapered having an 80 grit non slip finish. This puts the edges of the rod into the flesh of the surgeon's hands. These edges help the surgeon to resist the rotational forces which are created in the rod during the bending procedure.

Another advantage for the surgeon is the increased offset angle to 20° at the working ends. This allows the surgeon to criss-cross the benders and push them together or squeeze them with his fists. When working at waist level to exert almost full arm strength on the benders, it is easier to push together rather than pull apart.

Each of the above improvements enhance the surgeon's precision and the patient's safety. The combination of these improvements provide the surgeon with a major advancement in surgical techniques.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENT

Figure 1:
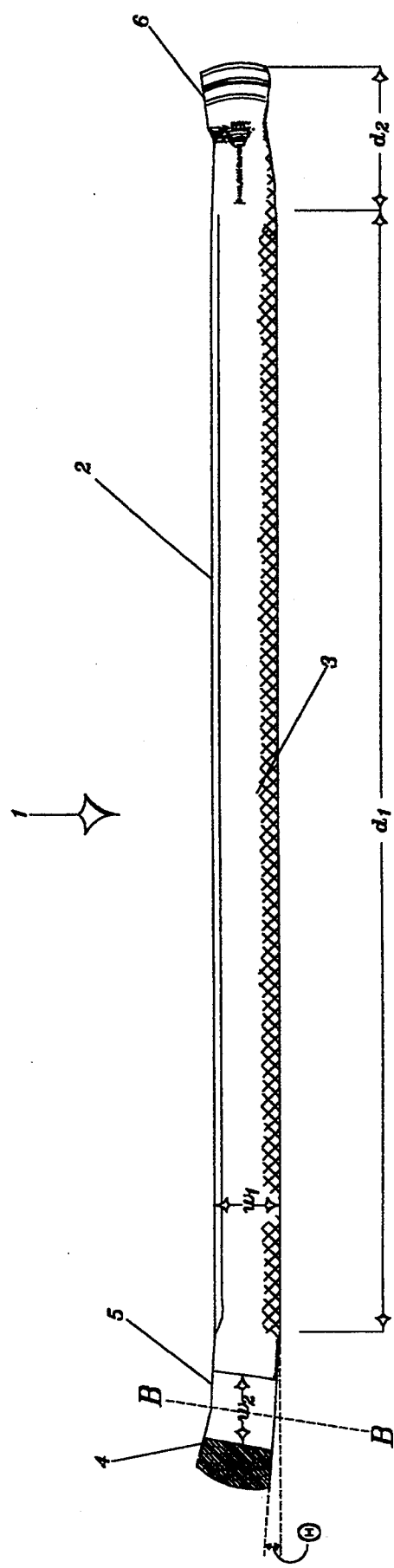
FIG. 1 (Prior art) is a side plan view of an Acromed Model 2060-30 in situ bender.
Figure 2:
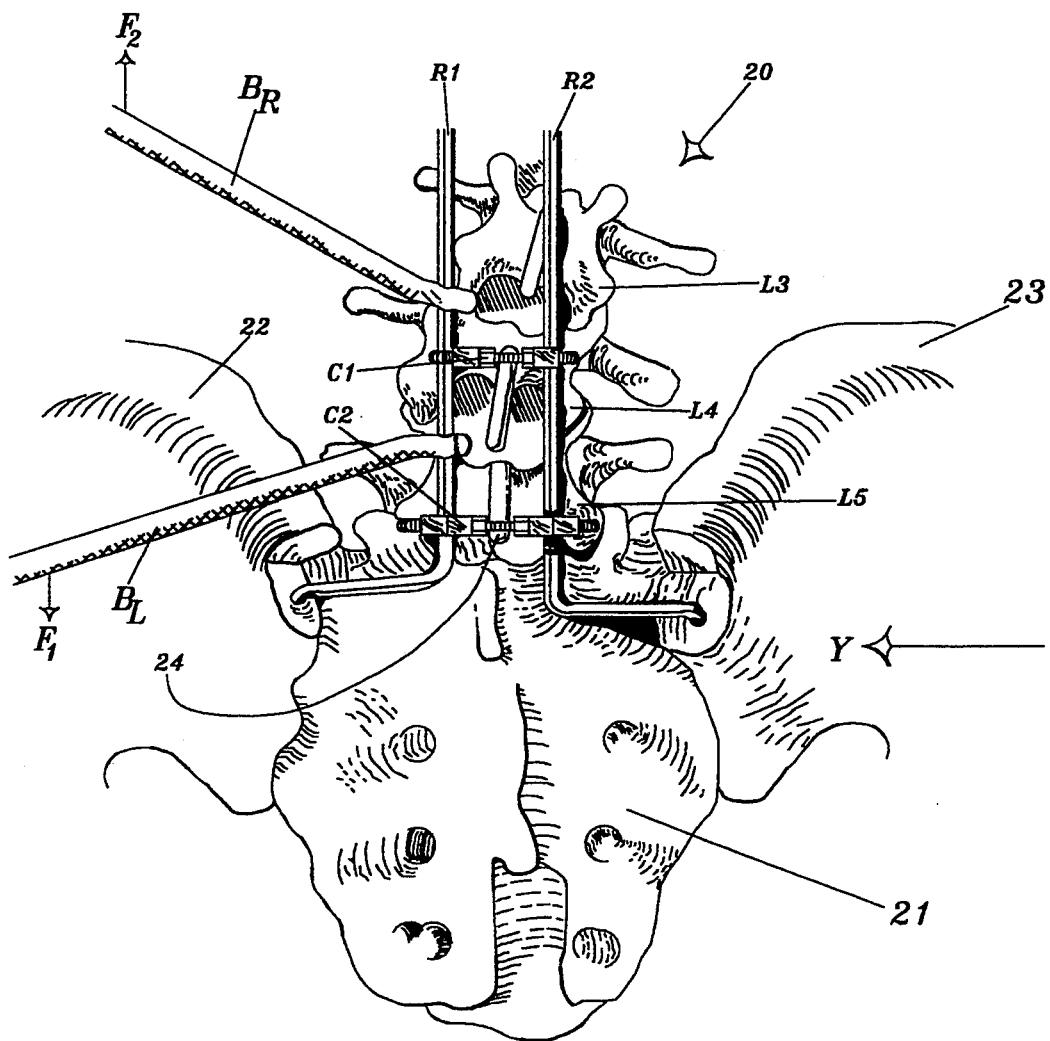
FIG. 2 is a top perspective view of a lower back during surgery showing a pair of in situ benders in operation.

Referring now to FIG. 2 a spine 20 is undergoing rod implant back surgery. The patient is lying on his stomach. The sacrum 21 and iliac crests 22, 23 are used to support the rods $R_1$, $R_2$ in a known manner. A hidden bone screw 24 in the lumbar L5 supports the clamp $C_2$. A clamp $C_1$ is secured in a similar manner to lumbar L4. Lumbar L3 lies above lumbar L4.

A pair of keyhole benders $B_L$, $B_R$ are performing in situ bending of the rod $R_1$ in the coronal (horizontal) plane. Spreading forces $F_1$, $F_2$ are applied by the surgeon located at position Y to keyhole benders $B_L$, $B_R$ to more precisely align rod $R_1$ with lumbar L3.

Figure 3:
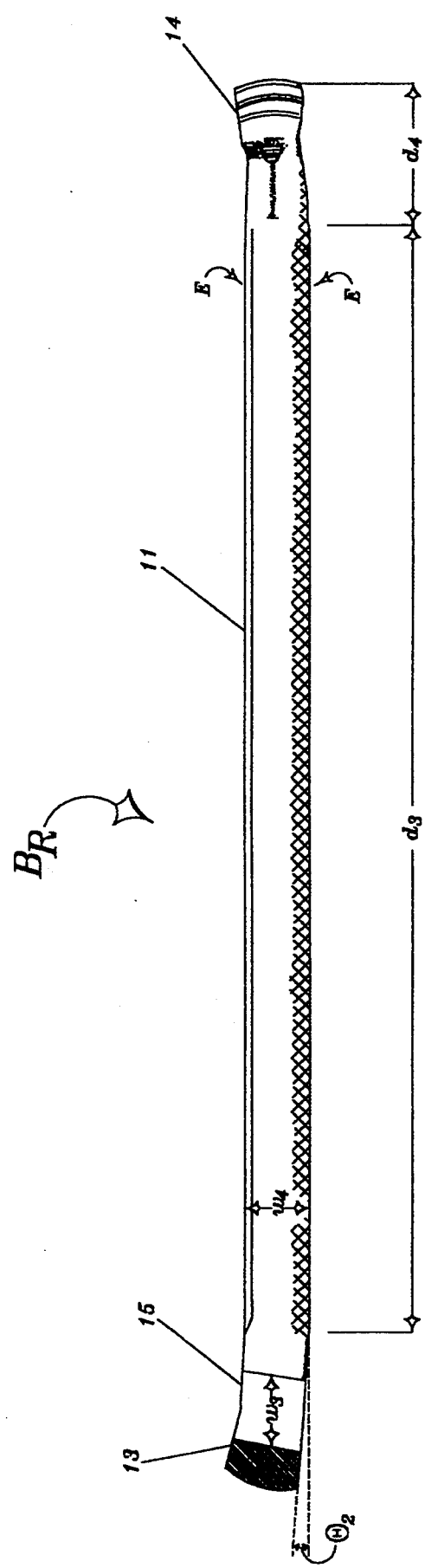
FIG. 3 is a side plan view of the keyhole rod bender.

Referring next to FIG. 3 the keyhole bender $B_R$ is used by the right hand of the surgeon in the procedure shown in FIG. 2. The handle 11 is flat, and the finish 12 is 80 grit on 304ss. The working ends 13, 14 are made of 440A hardenable stainless steel. A design choice would include a tool made completely out of one piece of 440A hardenable stainless steel. The rod slots 15, 16 are provided in the working ends 13, 14. The edges E help the surgeon to resist rotational torques on the handle 11.

Figure 4:
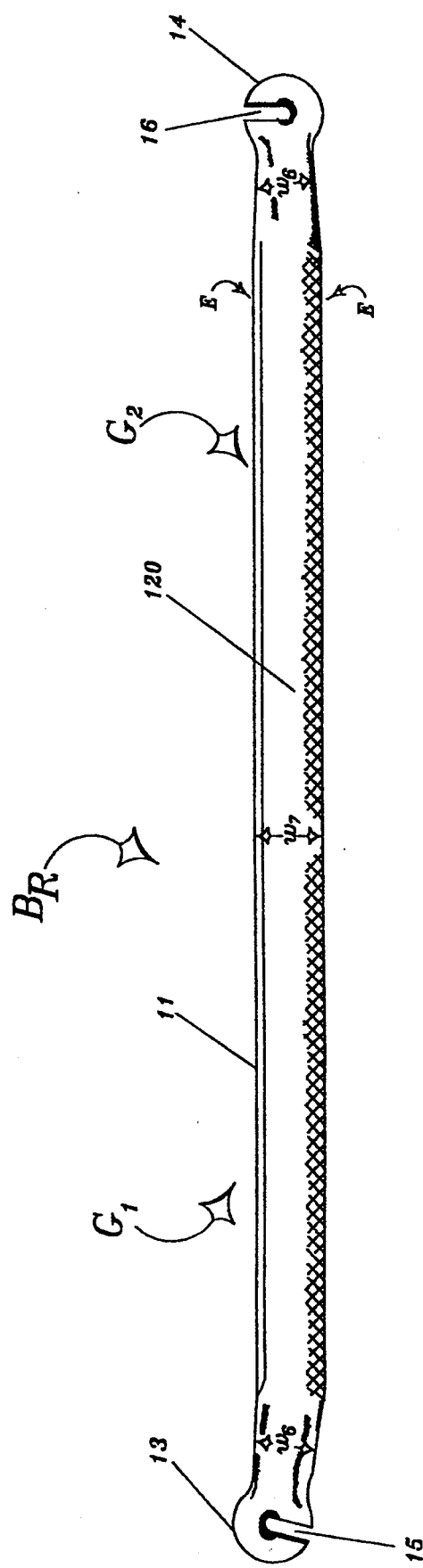
FIG. 4 is a top plan view of the keyhole rod bender of FIG. 3.

Other dimensions of keyhole bender $B_R$ are as follows:
$\theta_2 = 20° \pm 2°$
$W_3 = 0.260$ inch
$W_4 = \frac{3}{8}''$
$d_3 = 13\frac{1}{2}''$
$d_4 = \frac{3}{4}''$ In FIG. 4 is shown the taper of handle 11 from a center width W7 of $\frac{3}{4}''$ on the top surface 120 down to a working end width W6 of $\frac{3}{8}''$. This shape offers the surgeon a tapered grip at $G_1$ or $G_2$ if he desires.

Figure 5A:
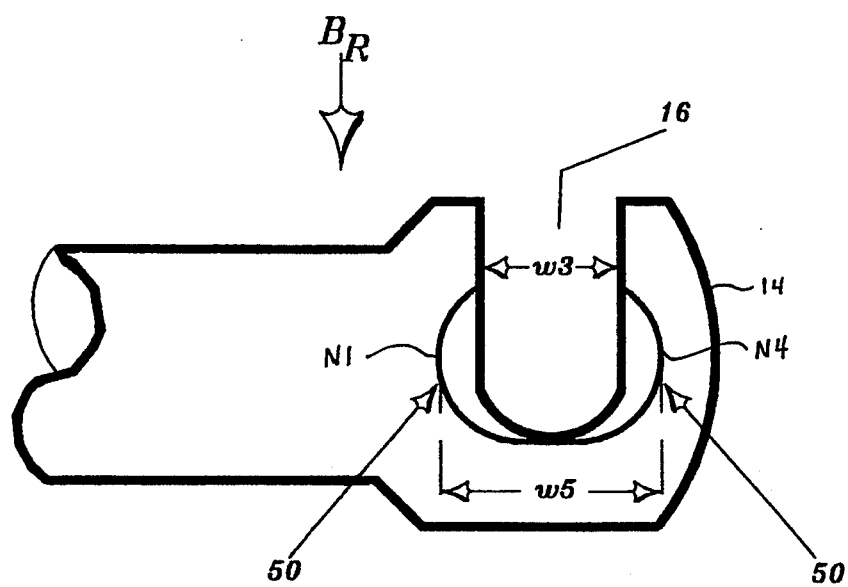
FIG. 5(a) is a side plan view of the keyhole rod slot of FIGS. 3,4.

In FIG. 5(a) the critical keyhole 50 is shown in rod slot 16. A boring drill has been used to create the keyhole 50 by boring two off axis bores in rod slot 16.

Figure 5B:
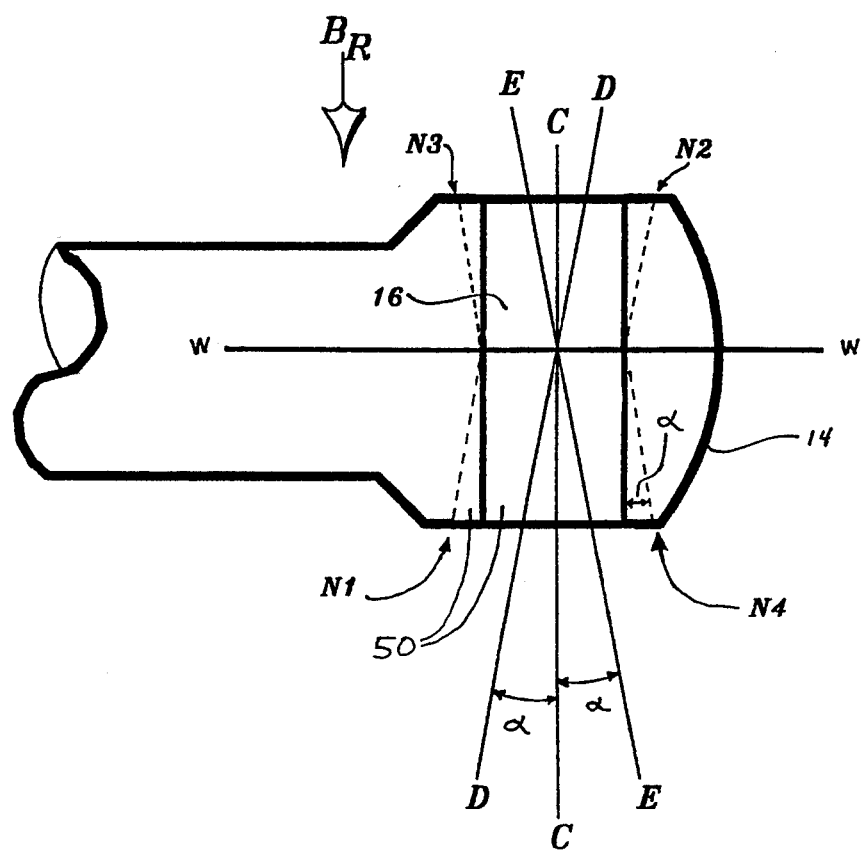
FIG. 5(b) is a top plan view of the keyhole rod slot of FIG. 5(a).

The central axis of rod slot 16 is shown as C—C in FIGS. 5(a), 5(b). Width W5 is 0.270 inch. To produce the opposing notches $N_1$, $N_2$ and the opposing notches $N_3$, $N_4$ the bender $B_R$ is drilled along axis D—D and axis E—E. Off axis D—D and E—E are each 3° (as shown by angle $\alpha$) off axis from central axis C—C. The axes C—C, D—D, E—E are all co-planar. Central axis C—C is at a 90° angle to the working end 14 axis W—W and co-planar therewith.

In operation during in situ bending the rod lodges at opposing notches $N_1$, $N_2$ or $N_3$, $N_4$ while the rod is under strain. It can be seen that these notches are only 0.005 inch deep at the surface. This equates to one half the difference between W5-W3. There exists about 1000 lbs. of indentation pressure at the notches. It is important to provide a shape of the notch as a frustum of a cone (indicated by dotted lines in FIG. 5(b)) in order to resist indenting the rod. This holding effect of the keyhole 50 by means of opposing notches $N_1$, $N_2/N_3$, $N_4$ greatly assists the surgeon to reduce the risk of accidentally pulling the rod out of the rod slot 16.

Figure 6:
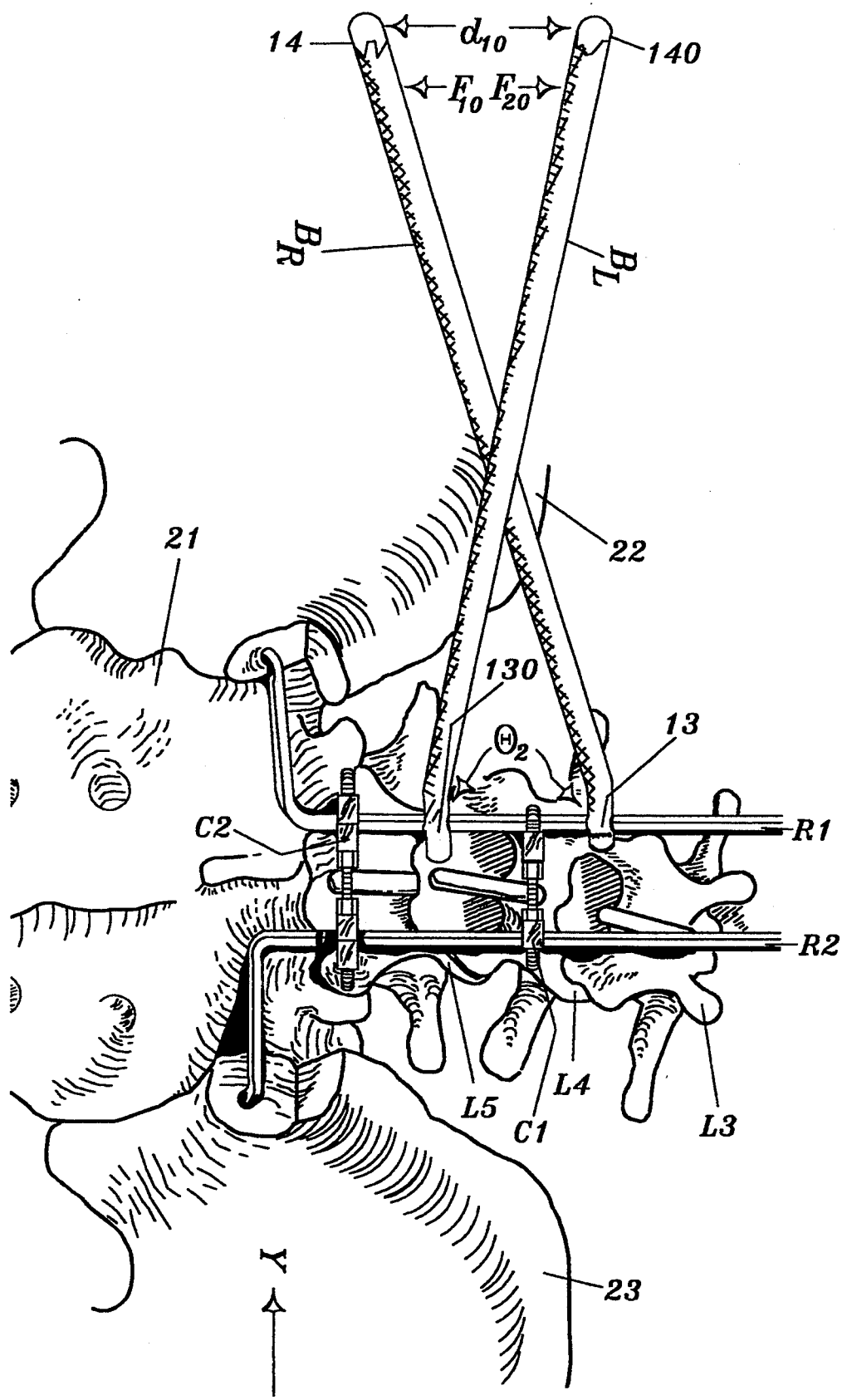
FIG. 6 is a top perspective view of a lower back during surgery showing a pair of keyhole rod benders in the criss-cross bending procedure.

Referring last to FIG. 6 the same surgeon as shown in FIG. 2 is now using a criss-cross method of pushing keyhole benders $B_L$, $B_R$ together. The angle $\theta_2$ allows a comfortable hand operating distance $d_{10}$ at the handle ends 14, 140 of the benders $B_L$, $B_R$. The working ends 13, 130 are bending rod $R_1$ in the opposite direction as that shown in FIG. 2.

For the surgeon operating at waist level it is easier for him to exert pushing forces $F_{10}$, $F_{20}$ instead of pulling forces $F_1$, $F_2$ as shown in FIG. 2.

We claim:

1. A first and second rod bender capable of plastically deforming a rod by movement relative to each other under an influence of force manually applied to end portions of said first and second rod benders, said first and second rod benders each comprising:
   a handle having a center;
   a working end at one end of said handle;
   said working end further comprising a working end central axis;
   said working end further comprising a rod slot having a bottom, a rod slot central axis, and a diameter; and
   said rod slot further comprising a keyhole hollow at the bottom formed substantially by a pair of offset bores, whereby the rod is held in a substantially static manner by opposing notches in the keyhole hollow.

2. The rod benders of claim 1 wherein said offset bores further comprise a 2° to 5° offset relative to the rod slot central axis and co-planar therewith.

3. The rod benders of claim 2 wherein said offset bores further comprise a diameter of about 0.005 inch wider than the rod slot diameter.

4. The rod benders of claim 1 wherein said rod slot central axis further comprises a 90° offset to said working end central axis.

5. The rod benders of claim 1 wherein said working end further comprises substantially a 20° offset to said handle.

6. The rod benders of claim 1 wherein said handle further comprises a flat shape having edges.

7. The rod benders of claim 6 wherein said handle further comprises a taper extending from a widest point at the center of the handle and narrowing to the working end.

8. The rod benders of claim 7 wherein said handle further comprises an 80 grit finish.

9. The rod benders of claim 1 wherein said handle is substantially $13\frac{1}{2}''$ long and the working end is substantially $\frac{3}{4}''$ long.

10. The rod benders of claim 1 further comprising a second working end located at an opposite end of the handle from said working end.

11. A first and second surgical rod bender capable of plastically deforming a surgically implanted rod in situ by movement relative to each other under an influence of force manually applied to end portions of said first and second rod benders, said first and second rod benders each comprising:
    a shaft having a central handle portion;
    a working end at each end of the shaft;
    said working ends each further comprising a rod slot having a bottom, a rod slot central axis, and a diameter; and
    said rod slot further comprising a keyhole hollow at the bottom formed substantially by a pair of bores 2° to 5° offset relative to the rod slot central axis, whereby the rod is held in a substantially static manner by opposing notches in the keyhole hollow.

12. The rod benders of claim 11 wherein said working ends further comprise a 20° offset to said shaft.

13. The rod benders of claim 11 wherein said offset bores further comprise a diameter of about 0.005 inch wider than the rod slot diameter.

14. The rod benders of claim 11 wherein said central handle portion further comprises a flat shape having edges.

15. The rod benders of claim 14 wherein said central handle portion further comprises a taper extending from a widest point at a midpoint of the central handle portion and narrowing to each working end.

16. A pair of rod benders each comprising:
a shank;
a working end at one end of the shank;
said working end further comprising a rod slot having a rod slot central axis 90° offset to the working end;
said rod slot further comprising a diameter to accommodate a rod, and a bottom; and
said rod slot bottom further comprising a keyhole hollow formed substantially by a pair of offset bores, whereby the rod is held in a substantially static manner by opposing notches in the keyhole hollow.

17. The rod benders of claim 16 wherein said offset bores further comprise a 2° to 5° offset relative to the rod slot central axis and co-planar therewith.

18. The rod benders of claim 17 wherein said offset bores further comprise a diameter of about 0.005 inch wider than the rod slot diameter.

* * * * *